United States Patent [19]
Abuto et al.

[11] Patent Number: 5,458,592
[45] Date of Patent: Oct. 17, 1995

[54] THERMOPLASTIC FIBROUS NONWOVEN WEBS FOR USE AS CORE WRAPS IN ABSORBENT ARTICLES

[75] Inventors: Frank P. Abuto, Alpharetta; Richard J. Schmidt, Roswell; Patrick E. O'Brien, Woodstock, all of Ga.; Michael W. Veith, Oshkosh; Anthony J. Wisneski, Kimberly, both of Wis.

[73] Assignee: Kimberly-Clark Corporation, Neenah, Wis.

[21] Appl. No.: 269,261

[22] Filed: Jun. 30, 1994

[51] Int. Cl.$^6$ .................................................... A61F 13/15
[52] U.S. Cl. ...................... 604/378; 604/367; 604/385.1; 156/167
[58] Field of Search .................................. 604/365, 367, 604/366, 378, 385.1; 156/167

[56] References Cited

U.S. PATENT DOCUMENTS

| | | | |
|---|---|---|---|
| Re. 32,957 | 6/1989 | Elias | 604/378 |
| 3,849,241 | 11/1974 | Butin et al. | 161/169 |
| 4,100,324 | 7/1978 | Anderson et al. | 428/288 |
| 4,587,154 | 5/1986 | Hotchkiss et al. | 428/195 |
| 4,604,313 | 8/1986 | McFarland et al. | 428/172 |
| 4,655,757 | 4/1988 | MacFarland et al. | 264/510 |
| 4,724,114 | 2/1988 | McFarland et al. | 264/510 |
| 4,838,885 | 6/1989 | Bernardin | 604/385.1 |
| 4,988,344 | 1/1991 | Reising et al. | 604/378 |
| 5,387,208 | 2/1995 | Ashton et al. | 604/385.1 |

FOREIGN PATENT DOCUMENTS

0598413A1 5/1994 European Pat. Off. .

2151272B 7/1985 United Kingdom .

OTHER PUBLICATIONS

NRL Report 4364, "Manufacture of Super–Fine Organic Fibers" by V. A. Wendt, E. L. Boone and C. D. Fluharty, May 25, 1954 pp. 1–15.
NRL Report 5265, "An Improved Device For The Formation of Super–Fine Thermoplastic Fibers" by K. D. Lawrence, R. T. Lukas and J. A. Young, Feb. 11, 1959, pp. 1–8.
ASTM D 5035–90—Standard Test Method For Breaking Force and Elongation of Textile Fabrics, Annual Book of ASTM Standards, vol. 7.01, pp. 726–731, Jan. 26, 1989.
ASTM F 316–86—Standard Test Method For Pore Size Characteristics of Membrane Filters by Bubble Point and Mean Flow Pore Test, Annual Book of ASTM Standards, vols. 11.01 and 14.02, Apr. 1986, pp. 818–823.
Federal Test Method Std. No. 191A–Method 5450—Permeability To Air; Cloth: Calibrated Orifice Method, Jul. 20, 1978.

*Primary Examiner*—Randall L. Green
*Assistant Examiner*—Dennis Ruhl
*Attorney, Agent, or Firm*—Patrick C. Wilson

[57] ABSTRACT

The present invention is directed to an absorbent article with a tissue-wrapped absorbent core wherein the tissue is made from a specifically designed thermoplastic fibrous nonwoven web which is particularly well-suited to trapping and retaining particulate material such as superabsorbent particles. The invention has particular application in conjunction with personal care products such as diapers, training pants, incontinence garments, sanitary napkins, bandages and the like.

16 Claims, 5 Drawing Sheets

THERMOPLASTIC FIBROUS NONWOVEN WEBS FOR USE AS CORE WRAPS IN ABSORBENT ARTICLES

FIELD OF THE INVENTION

The present invention is directed to an absorbent article with a tissue-wrapped absorbent core for use in personal care absorbent products and the process for making such meltblown tissue wrapped absorbent cores. The tissue wrap is made from thermoplastic fibers.

BACKGROUND OF THE INVENTION

The designs of personal care absorbent products have gone through extensive changes in recent times. Personal care absorbent products include such items as diapers, training pants, incontinence garments, sanitary napkins, bandages and the like. A major thrust in the design of these products, especially with diapers, training pants, incontinence garments and sanitary napkins, has been a reduction in the size of the products while increasing their absorptive capacity. Greater and greater usage of superabsorbents has made this possible.

Using diapers as an example, originally diapers were very thick in design due to the high volumes of fluff or wood pulp used to form the absorbent core of the diaper. As a result, the diapers were very bulky and they tended to leak because, as the absorbent fluff was wetted with urine, the fluff tended to collapse. Typically the fluff used in such personal care absorbent products had a liquid gram per gram capacities of 4 to 20 grams of aqueous liquid absorbed per gram of fluff. In addition, this capacity was dependent upon the amount of pressure being applied to the wet fluff. For example, at a pressure of 0.5 pounds per square inch (psi) the fluff would only hold approximately 7 grams per gram. At 0.1 psi the capacity would increase to approximately 12 grams per gram and at zero psi the capacity would be approximately 20 grams of liquid per gram of fluff.

With the advent of superabsorbents and their incorporation into absorbent cores, the size of the absorbent cores have been reduced. Initial superabsorbents had gram per gram capacities in the range of 50 grams per gram but the particles became very mushy when wet and would often cause gel blocking. Today, superabsorbents have higher absorbency while under load but to do this, many of the superabsorbents have had their capacities reduced to around 35 grams per gram. The first commercial diapers using superabsorbents incorporated from about 10 to 20 percent by weight superabsorbent, based upon the total weight of the absorbent core. The superabsorbent particles, which typically had 20 to 1,000 micron diameters, were contained within the absorbent cores through mechanical entanglement with the wood pulp fibers. In addition, paper tissue was sometimes wrapped around the superabsorbent-containing batts and sometimes the tissue was glued to itself and/or the fluff to further encapsulate and retain the fluff and superabsorbent.

Today, personal care absorbent products such as diapers have greatly reduced their thickness by removing large quantities of the fluff and replacing it with higher and higher percentages of superabsorbent particles. Some of the diapers today have absorbent cores with over 40 percent superabsorbent. Oftentimes the absorbent cores are compressed to further reduce their thickness after adding the tissue wrap. As a result, while old fluff cores tended to collapse when wetted, the new absorbent cores with superabsorbent tend to swell as they are wetted. This swelling coupled with the twisting and flexing the absorbent core experiences during use, can cause the paper tissue wrap to rip and tear, especially when wetted. When this happens, there is a greater chance that the superabsorbent will escape from the diaper. While this is not dangerous, it is not desirable from an overall product performance standpoint.

In the dry state, there is also greater potential for loss of the superabsorbent from the absorbent core as the percentages of superabsorbent are increased. With less fluff in the core, there is less mechanical entrapment of the fibers. Thus, if there is a rip in the paper tissue wrap or a portion of the glued seam becomes separated, there is a higher likelihood that some of the superabsorbent particles will escape. An even bigger problem is that the pores in many paper tissue wraps are too big and therefore allow the superabsorbent to escape. Consequently, there is a need for a more effective way of encapsulating the absorbent core.

From a processing standpoint there are also problems. Gluing a paper tissue wrap is messy and adds cost. Shake out of the superabsorbent particles can also cause equipment and housekeeping problems and higher production costs due to wasted material. As a result, there is a need for an improved absorbent core/wrap for uses such as in personal care absorbent products.

SUMMARY OF THE INVENTION

The present invention is directed to an absorbent article with a tissue-wrapped absorbent core made from thermoplastic fibers for use in personal care absorbent products such as diapers, training pants, incontinence garments, sanitary napkins, bandages and the like. The core wrap is made from a fibrous nonwoven web comprising a plurality of thermoplastic fibers. The core wrap has a plurality of pores with a mean flow pore size less than about 30 microns and wherein no more than 5 percent of the plurality of pores have a pore size greater than 50 microns. The core wrap has a wet to dry tensile strength ratio at peak load in the machine direction or the cross-machine direction of 0.5 or greater. In addition, the core wrap has a Frazier air permeability of at least 200 cubic feet per square foot per minute, a machine direction elongation at peak load of 30 percent or less, and a cross-machine direction elongation at peak load of 40 percent or less. The fibrous nonwoven core wrap is used to envelope an absorbent core including particulate superabsorbent. Due to the nature of the construction of the core wrap, less than 60 milligrams of shake up of particulate superabsorbent will occur. In addition, if so desired, the absorbent core may contain a plurality of fibers which are thermally bondable to the fibrous nonwoven web core wrap. To insure the proper retention of the particulate superabsorbent, it is desirable that at least 85 percent of the plurality of fibers forming the core wrap have fiber diameters of 8 microns or less and more desirably where at least 95 percent of such fibers have fiber diameters of 7 microns or less. Where particularly fine superabsorbent particles are being used, it is desirable that the plurality of pores in the fibrous nonwoven web core wrap with pore sizes greater than 50 microns be restricted to one percent or less.

The absorbent article including the fibrous nonwoven web core wrap and an absorbent core including particulate superabsorbent may be used by itself as a finished product or it may be incorporated into a personal care product. Such personal care products typically include a top sheet and a bottom sheet with some type of absorbent material disposed between the top and bottom sheets. In accordance with the present invention, the absorbent material is the previously described absorbent article.

A suitable process for forming an absorbent article according to the present invention includes forming a fibrous nonwoven web core wrap by extruding a molten thermoplastic polymer into a plurality of molten streams. These molten streams are then attenuated into a plurality of fibers which are deposited onto a forming surface to form a fibrous nonwoven web core wrap having a plurality of pores with a mean flow pore size of less than about 30 microns with no more than 5 percent of the plurality of pores having a pore size greater than 50 microns and with the fibrous nonwoven web core wrap having a wet to dry tensile strength ratio at peak load in the machine direction or cross-machine direction of 0.5 or greater and a Frazier air permeability of at least 200 cubic feet per square foot per minute. Once the fibrous nonwoven web core wrap has been formed, there is deposited thereon a quantity of particulate superabsorbent after which the core wrap is sealed to envelope the particulate superabsorbent. In addition, if so desired, a plurality of absorbent fibers may be deposited onto the core wrap prior to the sealing step.

DETAILED DESCRIPTION OF THE INVENTION

Figure 1:
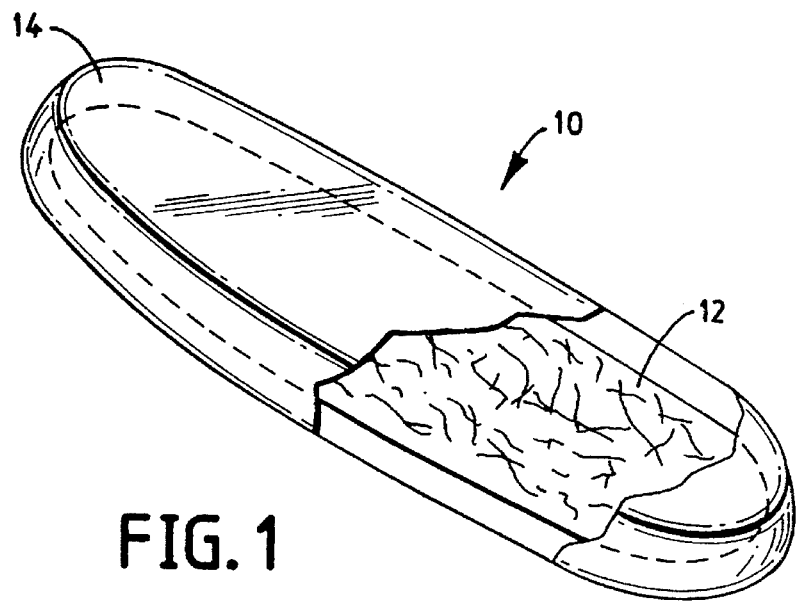
FIG. 1 is a perspective view of an absorbent article according to the present invention.

Referring to FIGS. 1 through 4, the present invention is directed to an absorbent article 10 including an absorbent core 12 and a core wrap 14. The core wrap 14 is particularly well-suited for containing absorbent cores which are made partially or completely from particulate matter such as superabsorbent particles. It should be understood, however, that the present invention is not restricted to use with superabsorbent particles but any particulate material such as odor absorbing and ion exchange resin particles and controlled release agents such as moisturizers, emollients and perfumes which require retention.

A "superabsorbent or superabsorbent material" refers to a water-swellable, water-soluble organic or inorganic material capable, under the most favorable conditions, of absorbing at least about 20 times its weight and, more desirably, at least about 30 times its weight in an aqueous solution containing 0.9 weight percent sodium chloride. Organic materials suitable for use as a superabsorbent material in conjunction with the present invention can include natural materials such as agar, pectin, guar gum, and the like; as well as synthetic materials, such as synthetic hydrogel polymers. Such hydrogel polymers include, for example, alkali metal salts of polyacrylic acids, polyacrylamides, polyvinyl alcohol, ethylene maleic anhydride copolymers, polyvinyl ethers, methyl cellulose, carboxymethyl cellulose, hydroxypropylcellulose, polyvinylmorpholinone; and polymers and copolymers of vinyl sulfonic acid, polyacrylates, polyacrylamides, polyvinylpyrridine, and the like. Other suitable polymers include hydrolyzed acrylonitrile grafted starch, acrylic acid grafted starch, and isobutylene maleic anhydride polymers and mixtures thereof. The hydrogel polymers are preferably lightly crosslinked to render the materials substantially water insoluble. Crosslinking may, for example, be accomplished by irradiation or by covalent, ionic, van der Waals, or hydrogen bonding. The superabsorbent materials may be in any form suitable for use in absorbent composites including particles, fibers, flakes, spheres, and the like. Such superabsorbents are usually available in particle sizes ranging from about 20 to about 1000 microns. The absorbent core 12 can contain from 0 to 100 percent superabsorbent by weight based upon the total weight of the absorbent core.

Typically an absorbent core 12 for a personal care absorbent product will include superabsorbent particles and, optionally, additional absorbent material such as absorbent fibers including, but not limited to, wood pulp fluff fibers, synthetic wood pulp fibers, synthetic fibers and combinations of the foregoing. Wood pulp fluff such as CR-54 wood pulp fluff from Kimberly-Clark Corporation of Neenah, Wis. is an effective absorbent supplement. A common problem with wood pulp fluff, however, is its lack of integrity and its tendency to collapse when wet. As a result, it is often advantageous to add a stiffer reinforcing fiber into the absorbent core 12 such as polyolefin meltblown fibers or shorter length staple fibers. Such combinations of fibers are sometimes referred to as "coform". The manufacture of meltblown fibers and combinations of meltblown fibers with superabsorbents and/or wood pulp fibers are well known. Meltblown webs are made from fibers formed by extruding a molten thermoplastic material through a plurality of fine, usually circular dye capillaries as molten threads or filaments into a high-velocity heated air stream which attenuates the filaments of molten thermoplastic material to reduce their diameters. Thereafter, the meltblown fibers are carried by the high-velocity gas stream and are deposited on a collecting surface to form a web of randomly dispersed meltblown fibers. The meltblown process is well known and is described in various patents and publications, including NRL Report 4364, "Manufacture of Super-Fine Organic Fibers" by V. A. Wendt, E. L. Boone and C. D. Fluharty; NRL Report 5265, "An Improved Device For the Formation of Super-Fine Thermoplastic Fibers" by K. D. Lawrence, R. T. Lukas and J. A. Young; and U.S. Pat. No. 3,849,241, issued Nov. 19, 1974 to Buntin et al. To form "coform" materials, additional components are mixed with the meltblown fibers as the fibers are deposited onto a forming surface. For example, superabsorbent particles and/or staple fibers such as wood pulp fibers may be injected into the meltblown fiber stream so as to be entrapped and/or bonded to the meltblown fibers. See, for example, U.S. Pat. No. 4,100,324 to Anderson et al.; U.S. Pat. No. 4,587,154 to Hotchkiss et al., U.S. Pat. Nos. 4,604,313; 4,655,757 and 4,724,114 to McFarland et al. and U.K. Patent GB 2,151,272 to Minto et al., all of which are incorporated herein by reference in their entirety.

The core wrap of the present invention is a specifically designed and engineered fibrous nonwoven web made from fine diameter thermoplastic fibers with particular pore sizes and air permeability. By thermoplastic fibers it is meant fibers which are formed from polymers such that the fibers can be bonded to themselves using heat or heat and pressure. While not being limited to the specific method of manufacture, meltblown fibrous nonwoven webs have been found to work particularly well. With respect to polymer selection, polyolefin fibers and especially polypropylene-based polymers have been found to work well. The general manufacture of such meltblown fibrous nonwoven webs is well known. See for example, the previously mentioned meltblown patents referred to above. The fibers may be hydrophilic or hydrophobic, though it is desirable that the resultant web/core wrap be hydrophilic. As a result, the fibers may be treated to be hydrophilic as by the use of a surfactant treatment.

In order to function well as a core wrap, the meltblown web should have certain specific properties. A common problem with paper tissue wrap is that it has inadequate strength in the wet state. Typically a paper tissue wrap will have a wet to dry strength ratio in either the machine direction (MD) or cross-machine direction (CD) as measured by the test method outlined below of less than 0.5. In contrast, the absorbent core wrap 14 of the present invention will have wet to dry strength ratios above 0.5 and sometimes 1.0 or higher. In addition, the mean flow pore size as measured by the test below should be about 30 microns or less and less than five percent of the total pores for any given area should be 50 microns or greater. More desirably, less than one percent of the total pores for a given area should be 50 microns or greater. To accomplish this it is desirable that at least 85 percent of the fibers of the core wrap 14 have fiber diameters of 8 microns or less and more desirably at least 95 percent of the fibers should have fiber diameters of 7 microns or less. As a result, the absorbent core wrap 14 will have a Frazier air permeability of 200 cubic feet per square foot per minute or greater. Once the absorbent core 12 has been wrapped with the core wrap 14, the wrap 14 should not unduly expand or stretch as this might cause the pores to enlarge and allow excessive particulate matter to escape. Consequently, the core wrap, while in the dry state, should have respective elongation values at peak load in the machine and cross machine directions of 30 percent or less and 40 percent or less.

Figure 5:
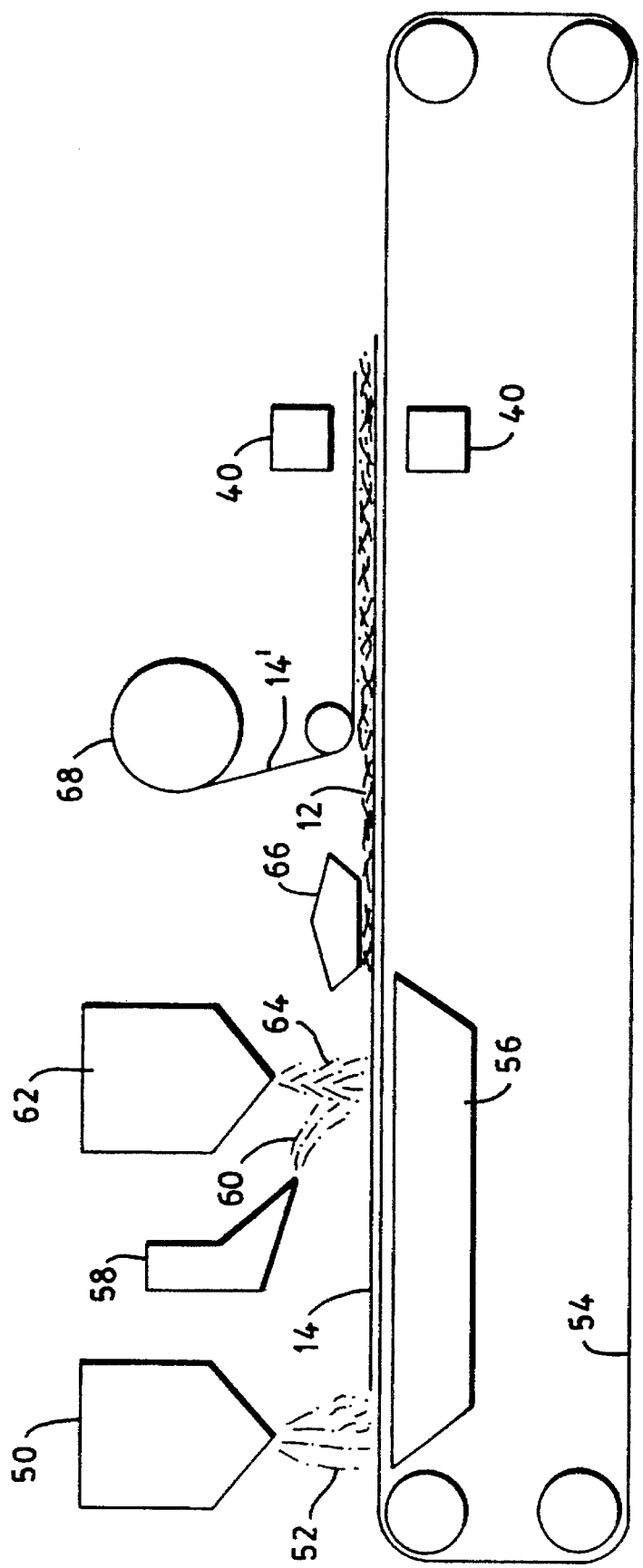
FIG. 5 is a schematic side view of a process for forming an absorbent article according to the present invention.

To form the present invention, reference is made to the process depicted schematically in FIG. 5. First an absorbent core wrap 14 must be formed using a fiber forming apparatus 50 which, in this case, is a meltblown apparatus. As shown in FIG. 5, the meltblown tissue wrap is formed in-line, however, it is also possible to form the meltblown tissue wrap off-line and then feed it into the process of FIG. 5 in roll form. Returning to FIG. 5, a molten thermoplastic polymer such as a polyolefin is heated and then extruded through a die tip to form a plurality of molten streams of polymer. As the streams of polymer leave the die tip of the meltblown apparatus 50, they are attenuated by high velocity air which draws the molten streams into a plurality of fibers 52 which are deposited onto a forming surface 54 in a random entangled web to form the core wrap 14. To further assist in the web formation and to impart better hold-down of the web onto the forming surface 54, a vacuum 56 may be used underneath the foraminous forming surface 54.

Once the absorbent core wrap 14 has been formed on the forming surface 54 or unrolled from a preformed roll (not shown), the absorbent core 12 must be formed or deposited onto the surface of the absorbent core wrap 14. As shown in FIG. 5, there is a source 58 of superabsorbent or other type particles 60 and an optional source 62 of absorbent fibers 64 such as, for example, wood pulp fibers or meltblown fibers. If both absorbent fibers 64 and superabsorbent particles 60 are to be used to form the absorbent core 12, they may be intermixed before they are deposited onto the absorbent core wrap 14 as shown in FIG. 5 or they may be layered so as to isolate the particles within the interior of the absorbent core 12. Again to further assist in the deposition and retention of the absorbent core materials onto the surface of the absorbent core wrap 14, the same vacuum source 56 or a separate source if so desired may be used.

After the absorbent core 12 has been deposited onto the absorbent core wrap 14, the core wrap 14 should be sealed around the absorbent core 12 so as to envelope the absorbent core 12 and form an absorbent article 10. As shown by FIGS. 1 through 4, to envelope the absorbent core, the core wrap 14 should completely wrap around the core 12 and be sealed, preferably to itself. It is also desirable that the ends of the absorbent article also be sealed. Due to the thermoplastic nature of the fibers of the core wrap 14, the core wrap 14 may be heat sealed to itself thus avoiding the need for glue though glue can also be used if so desired. In addition, if so desired, the absorbent core materials 60 and 64 may be cycled on and off so that end seals can be formed in between the deposits of core material. Further, if the absorbent fibers 64 are also thermoplastic in nature, end and side seals can be made in the core wrap 14 which bond right through the absorbent core 12.

Figure 2:
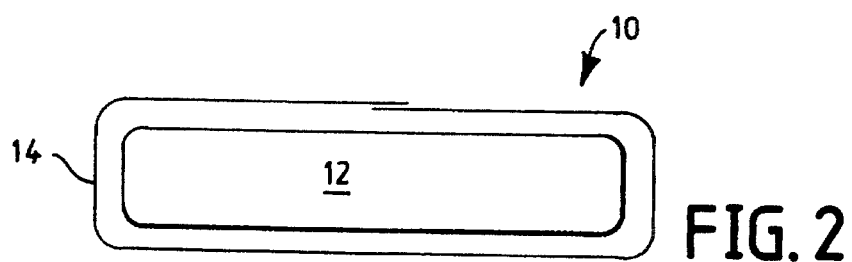
FIG. 2 is a cross-sectional side view of an absorbent article according to the present invention.
Figure 3:
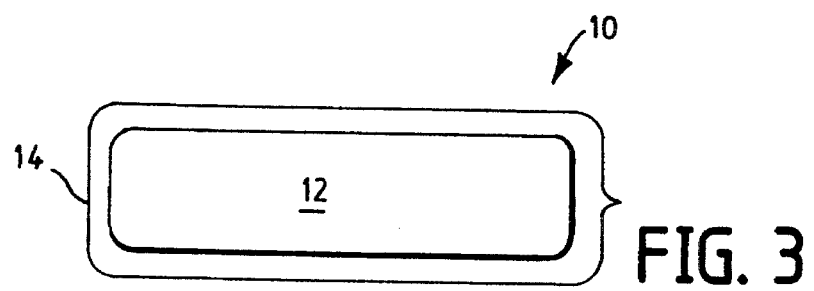
FIG. 3 is a cross-sectional side view of another absorbent article according to the present invention.
Figure 4:
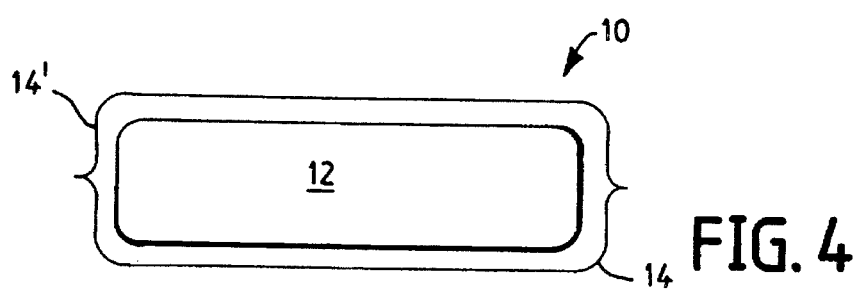
FIG. 4 is a cross-sectional side view of yet another absorbent article according to the present invention.

As shown in FIGS. 2 and 3 of the drawings, if the core wrap 14 is sufficiently wide, it may be folded over on itself and then sealed using, for example, adhesives, heat and/or pressure either on top or bottom (FIG. 2) or on the side (FIG. 3) of the absorbent article 10. The folding of the core wrap 14 over onto itself can be accomplished through the use of conventional sheet folding means 66 such as curved plates which work the core wrap 14 over onto itself. Alternatively, a separate sheet of core wrap 14' may be unrolled or formed from a second source 68 so as to encapsulate the absorbent core 12 between a first sheet of absorbent core wrap 14 and a second sheet of absorbent core wrap 14'. See FIG. 4. As with the embodiments shown in FIGS. 2 and 3, the loose edges of the core wrap may be sealed together using a sealing means 70 such as an ultrasonic bonder or other thermomechanical bonding means or through the use of adhesives.

Figure 6:
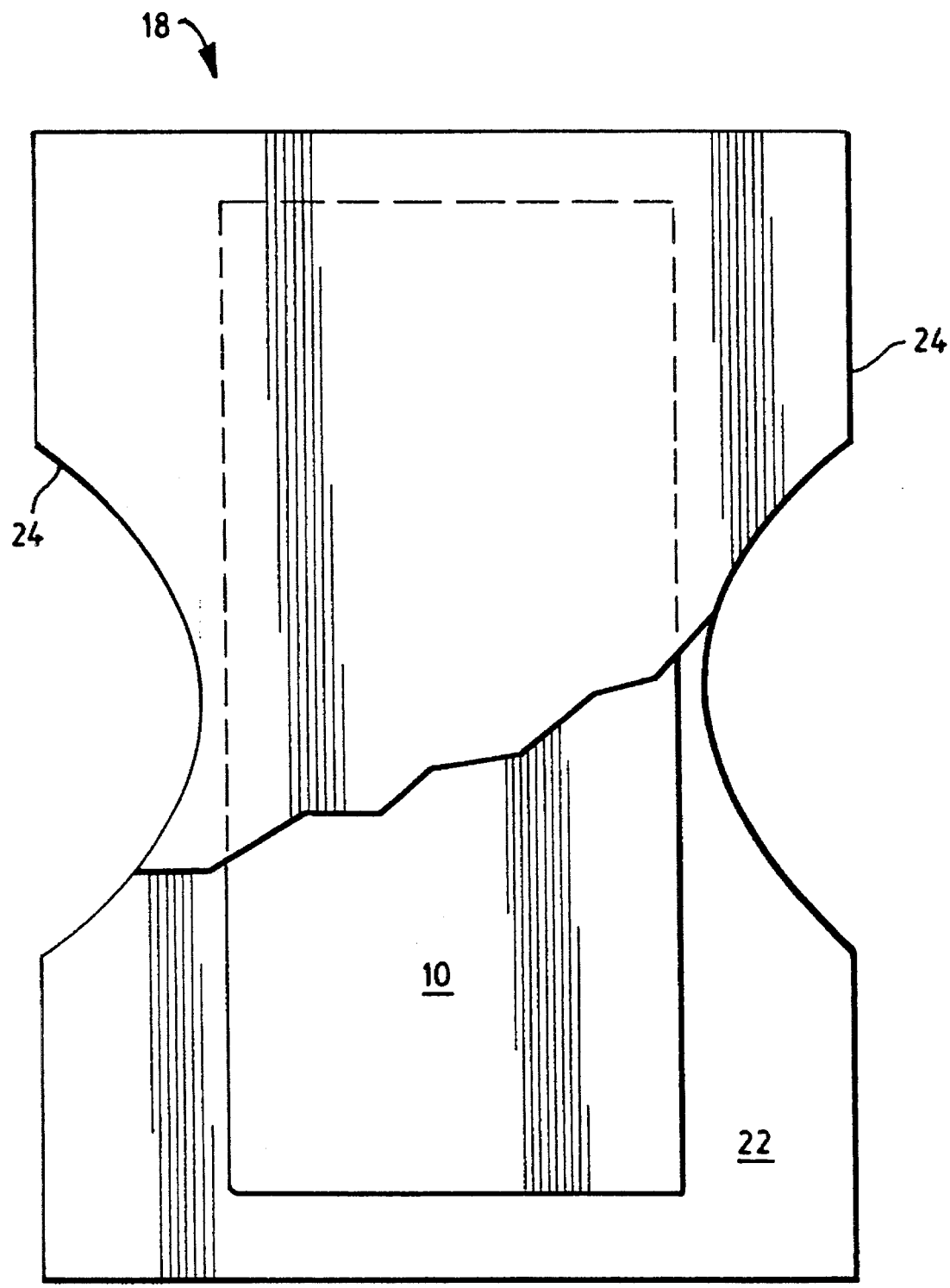
FIG. 6 is a partial cut-away top plan view of a personal care absorbent product including an absorbent article according to the present invention.

The absorbent article 10, once formed, may be used by itself or it may be incorporated into a personal care absorbent product 18 such as is shown in FIG. 6. For purposes of illustration only, the personal care absorbent product 18 shown in FIG. 6 is in the form of a diaper. This should be considered illustrative only as the absorbent article 10 of the present invention may be used in all types of personal care absorbent products including, but not limited to, diapers, training pants, incontinence garments, sanitary napkins, bandages and the like.

All such personal care absorbent products generally include a liquid permeable top sheet 20 and a generally liquid impermeable bottom sheet 22. Disposed between the top sheet 20 and the bottom sheet 22 there is an absorbent material and, in the present application, it is the absorbent article 10. If desired, the top sheet 20 and bottom sheet 22 may be sealed to one another about their respective peripheries 24 so as to encase the absorbent article 10.

Having thus described the present invention and the process for making it, a series of examples were prepared to further illustrate the present invention. These examples and the test procedures for measuring them are set forth below.

TEST PROCEDURES

Coulter Porometer Mean Flow Pore Size and Pore Size Distribution Test

A Coulter 115/60 porometer from Coulter Electronics, Ltd. of Luton, England was used to determine mean flow pore size, maximum flow pore size and pore size distribution. The apparatus was capable of measuring pore sizes up to 300 microns. Determinations of the mean flow pore size, maximum flow pore size and pore size distribution were made in accordance with ASTM Standard Test Methods Designation F316-86 for Pore Size Characteristics of Membrane Filters by Bubble Point And Mean Flow Pore Test.

Frazier Air Permeability

The procedure used to determine Frazier air permeability was conducted in accordance with the specifications of method 5450, Federal Test Methods Standard No. 191 A, except that specimen sizes were 8 inches×8 inches rather than 7 inches×7 inches. The larger size made it possible to ensure that all sides of the specimen extended well beyond the retaining ring and facilitated clamping of the specimen securely and evenly across the orifice. Values were given in cubic feet per square foot per minute (ft$^3$/ft$^2$/min). To convert to cubic centimeters per square centimeter per minute multiple by 30.5.

Tensile Strength (wet and dry) and Elongation

ASTM procedure D 5035-90—Standard Test Method for Breaking Force and Elongation of Textile fabrics (Strip Force) was used to measure the wet and dry tensile strengths to peak load. A SinTech model S2, constant-rate-of-extension type testing machine manufactured by SinTech Corporation of Carey, N.C. was used for the procedure. Three inch (75 mm) cut strip samples were used instead of the one inch (25 mm) or two inch (50 mm) samples specified in procedure D 5035-90.

Fiber Diameter

The fibers of sample nonwoven webs were sputter coated with gold in preparation for examination with a Scanning Electron Microscope (SEM) such as a Cambridge Stereoscan 200 microscope from Leica, Inc.of Deerfield, Ill. One hundred fibers were selected at random and individual fiber diameters were measured using the electronic cursors of the SEM. Particular care should be taken not to select fibers which have been fused together.

Shake Box Shake-Out Test Procedure

Sample Preparation

Figure 8:
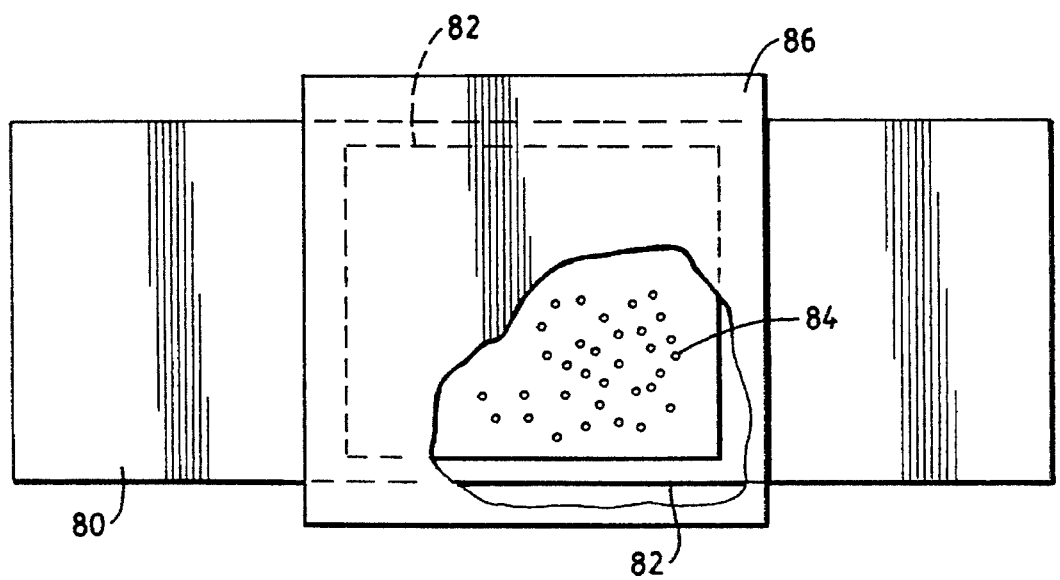
FIG. 8 is a partial cut-away, top plan view of a representative sample mount and test sample employed for shake-out testing.
Figure 9:
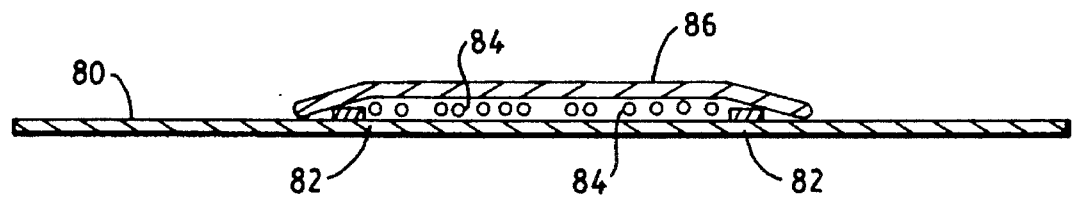
FIG. 9 is a side view of the sample mount and test sample shown in FIG. 8.

With reference to FIGS. 8 and 9, a 4 inch by 11 inch sample mount 80 was cut from a 350 gsm cellulose paper (or an equivalent material which provided suitable structural integrity with enough bending flexibility to allow an insertion of the sample mount 80 into the test unit).

A 0.25 inch wide, two-sided pressure sensitive adhesive tape 82, such as 3M Scotch™ brand 2 mil, high tack adhesive transfer tape (#465) or equivalent was applied to the center of the sample mount to form a square "window frame" having outside dimensions of 4 inch by 4 inch.

500 mg (±5 mg) of superabsorbent material 84 was placed in the center of the "window frame". The particle size distribution of the superabsorbent material was determined by conventional sieve analysis, and was as follows:

212–300 micrometers: 40% (by weight)

149–212 micrometers: 35%

90–149 micrometers: 25%

Testing was conducted on a single sheet of the sample core wrap 14, and a 4.5 inch by 4.5 inch piece 86 of the sample being tested was placed over the framed area and adhered by pressing the sample onto the adhesive tape to provide a tight seal.

Shake Test Unit

Figure 7:
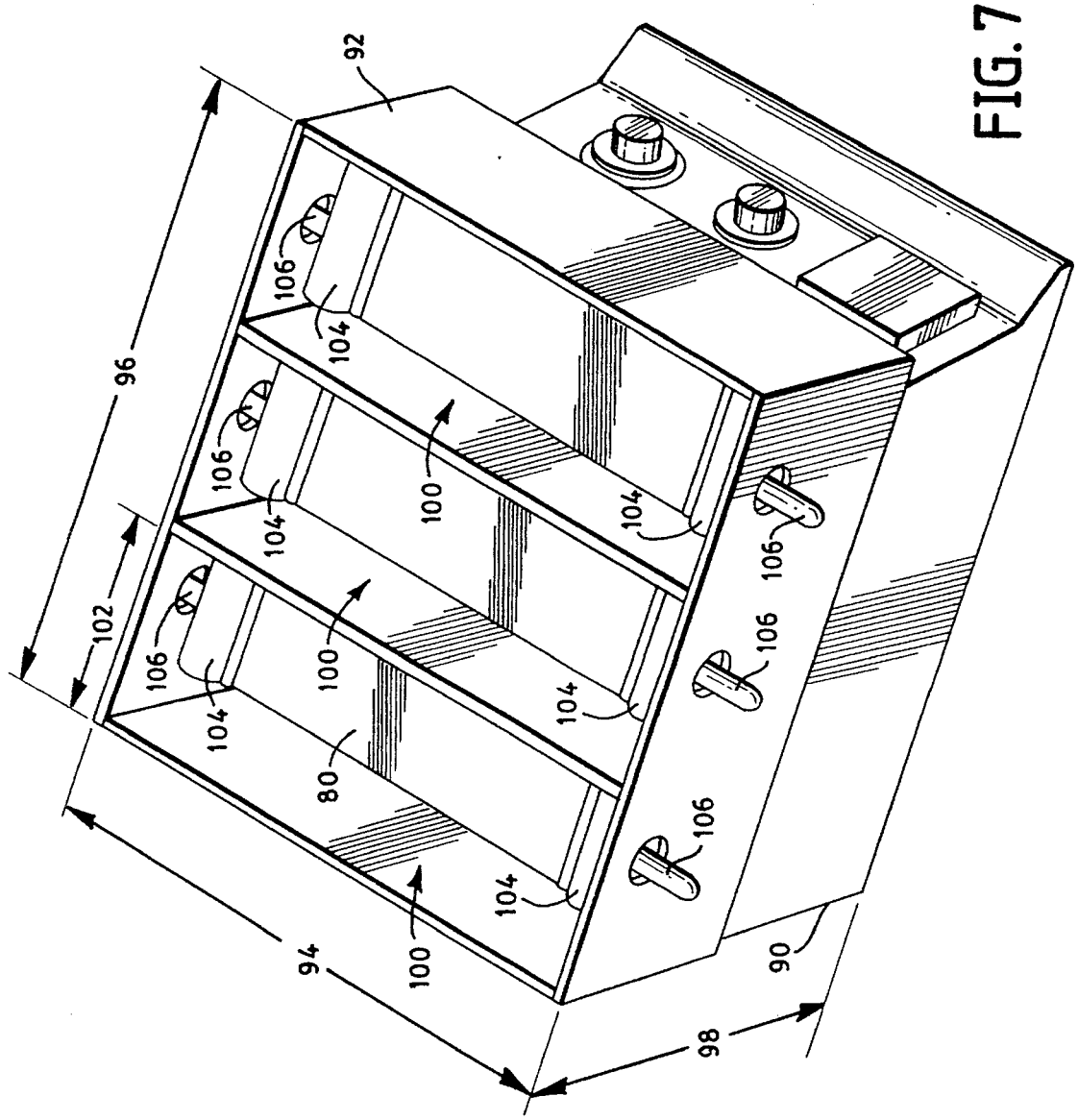
FIG. 7 is a perspective view of a shake-out testing apparatus.

With reference to FIG. 7, a shaker mechanism 90, such as a Variable Junior Orbit Shaker (Model 3520) available from Lab-Line, was used to determine the ability of the core wrap to contain superabsorbent. Alternatively, an equivalent shaker may be employed.

A testing box 92 was operably secured to the shaker. The box 92 had four side walls and a cooperating bottom wall which were constructed of any suitable material such as clear polycarbonate sheet having a thickness of about 0.025 inch. The box measured approximately 11.5 inches along its length 94, by about 13 inches along its width 96, by 5 inches along its depth 98, and was sectionalized into three compartments 100, each of which was large enough to accommodate the placement of a sample mount therein. Accordingly, each of the shown compartments had inside measurements of approximately 4 inches by 11.5 inches. Each compartment was also equipped with two conventional spring clamps 104 which were positioned on opposed end walls of the compartment and constructed to securely hold the sample mounts in place. One jaw of each spring clamp was securely fastened to its corresponding compartment end wall and the other jaw was arranged to be free to open and close upon pressure applied to its associated activating lever 106. For testing, the opposite ends of a sample mount were securely held in a pair of clamps attached in the particular compartment employed for testing. The sample mount was positioned with the sample core wrap located closest to the bottom wall of the box. The shaker was turned on and operated at an indicated speed of 350 rpm for a period of 5 minutes.

Collection of Superabsorbent

The amount of superabsorbent which was shaken out through the sample core wrap was determined by a vacuum collection of debris. For examples 5 through 8, a 37 mm diameter air monitoring cassette (Gelman Science Product number 4338) was prepared by placing a 37 mm cellulose support pad (Product number 64747) in the bottom of the cassette. A 0.08 micrometer Metricel® membrane (Product number 64678) was placed on top of the support pad and the top of the cassette was pressed into the mating bottom. The prepared cassette was weighed and the weight was recorded or tared. The cassette was hooked to a suitable vacuum source with tubing. A plastic funnel was fitted to the tubing and the superabsorbent was vacuumed into the monitoring cassette. The cassette was reweighed and the amount of superabsorbent was determined by the weight differential. This test was used for examples 5 through 8 and values given in the claims should be calculated using this method.

Packet Shake-Out Test

A second method of testing was also used to determine particle shake-out from the absorbent core wraps. This test was used with respect to Examples 1 through 4 and 9. To perform the test an 8 inch by 4 inch sample of the core wrap was cut. Next 0.5 grams of Dow 534 particulate superabsorbent from the Dow Chemical Company was placed on top of the sample and the sample was folded over onto itself to cover the superabsorbent and form a 4 inch by 4 inch packet. The superabsorbent particles ranged in size from 88 to 149 microns. All four sides of the packet were then taped to a piece of plastic film. The tape overlapped approximately 0.25 inch the packet periphery. The sample and film were then inverted (packet side down) and the combination was attached to a Model RX-24 Shaker from the Tyler Company. Below the sample there was placed a tared pan of sufficient size to collect any superabsorbent shake-out. The shaker was turned on and operated for a period of five minutes. The shaker operated at approximately 520 cycles per minute with a 0.5 inch stroke. After five minutes the shaker was turned off and the pan was reweighed. The difference between the collected weight and the tared weight represented the amount of shake-out.

EXAMPLES

Example 1

A polypropylene meltblown fibrous nonwoven web core wrap was made using Himont PF-015 polypropylene polymer from Himont, USA of Wilmington, Del. The meltblown core wrap was made in accordance with meltblowing teachings described above utilizing a two bank meltblown apparatus. The polypropylene was extruded through the two bank meltblown die assembly at a throughput of 2.5 pounds per inch per hour (PIH). The extruded streams of molten polymer were attenuated with primary attenuation air delivered at a rate of between about 1700 and 2000 cubic feet per minute at a temperature of 530° F. The resultant meltblown core wrap had a basis weight of 8.0 grams per square meter (gsm) and was treated with Triton X-102 surfactant octylophenoxypolyethoxyethanol nonionic surfactant from Union Carbide Chemicals and Plastics Company, Inc., Industrial Chemicals Division of Danbury, Conn.

The core wrap had dry machine direction (MD) and cross-machine direction (CD) tensile strengths measured at peak loads of 1010 grams and 514 grams respectively and machine direction and cross-machine direction elongations at peak load of 16 and 33 percent respectively. The wet machine direction and cross machine direction tensile strengths at peak load were 998 grams and 554 grams respectively. The wet to dry tensile strength ratios in both the machine and cross machine directions were respectively 0.99 and 1.08. Ratios were determined by dividing wet and dry values for respective MD and CD directions. The mean flow pore size for the sample was 25 microns and the maximum flow pore size was 47 microns with 0.5 percent of the overall pores having a pore size greater than 50 microns. The core wrap had a Frazier air permeability of 361 cubic feet per square foot per minute. A sample of the meltblown core wrap was subsequently made into a packet and filled with 0.5 grams of Dow 534 type superabsorbent from the Dow Chemical Company of Midland, Mich. with particle sizes ranging between 88 and 150 microns in diameter. The packet was subjected to the packet shake test procedure as outlined above and the fallout was measured to be 2.7 milligrams as compared to 395 milligrams of fall-out for the same superabsorbent when placed within a packet made from standard paper tissue core wrap material.

Example 2

In Example 2 a polypropylene meltblown fibrous nonwoven web core wrap was made using the same polymer and surfactant treatments as listed above with respect to Example 1. The meltblown web was made using three banks of meltblown dies delivering polymer at a rate of 3.5 pounds per inch per hour (PIH) with the primary attenuation airflow remaining the same as that in Example 1. The resultant web had a basis weight of 11.0 grams per square meter. The core wrap had a dry machine direction tensile strength at peak load of 1391 grams. The mean flow pore size was 23 microns and the maximum flow pore size was 40 microns with zero percent of the pores being greater than 50 microns. Frazier air permeability was measured to be 250 cubic feet per square foot per minute. The meltblown core wrap was subsequently made into a packet and filled with 0.5 grams of the same Dow 534 type superabsorbent as mentioned in Example 1. The packet was then subjected to the shake test and fall out was measured to be 5.0 milligrams.

Example 3

In Example 3 an 8.0 gram per square meter basis weight polypropylene meltblown absorbent core wrap was made using the same polymer as in the previous examples. The core wrap had a dry MD tensile strength at peak load of 914 grams, a mean pore flow size of 24 microns and the maximum flow pore size was 40 microns with zero percent of the pores being greater than 50 microns. The Frazier air permeability was 327 cubic feet per square foot per minute and the core wrap had 1.1 milligrams of shake-out using the packet shake-out test.

Example 4

In Example 4 the same Himont polypropylene polymer was used to make a meltblown absorbent core wrap with a basis weight of 8.8 grams per square meter. The core wrap had an average fiber diameter of 2.4 microns, dry MD and CD tensile strengths at peak load of 844 and 382 grams, respectively, and MD and CD elongations of 15 percent and 11 percent, respectively. Mean flow pore size was 22 microns and the maximum flow pore size was 34 microns. The Frazier air permeability was 484 cubic feet per square foot per minute and the packet shake-out test yielded 0.4 milligrams of superabsorbent.

Example 5

In Example 5 a meltblown absorbent core wrap was made with the same Himont polypropylene polymer. Processing conditions included a throughput of 1.5 pounds per inch per hour with the use of attenuating air flowing at a rate of 580 cubic feet per minute at a temperature of 490° F. The forming distance between the meltblown die tip and the forming surface was 9.5 inches and the forming wire onto which the web was deposited was traveling at a rate of 204 feet per minute. The sample had a basis weight of 7.2 grams per square meter with an average fiber diameter of 2.6 microns with 97 percent of the fibers having fiber diameters below 7 microns. The wet and dry MD peak load tensile strengths were 556 grams and 584 grams respectively and the wet and dry CD peak load tensile strengths were 251 grams and 231 grams respectively. As a result, the wet to dry strength ratios in both the MD and CD directions were 0.95 and 1.09 respectively. The absorbent core wrap had dry elongation at peak load percentages in the MD and CD directions of 6 and 10 percent respectively. Frazier air permeability was measured to be 492 cubic feet per square foot per minute. Using the above described Coulter porometer pore size test, the mean flow pore size of the meltblown core wrap was 26 microns. Less than 5 percent of these pores were larger than 50 microns. Using the shake box shake-out test described above, the sample was found to have a shake out of 2.0 milligrams of superabsorbent. A comparative diaper tissue sample used by Kimberly-Clark Corporation will generally have MD and CD wet and dry peak load ensile strength ratios much less than 0.5 in either direction. The Frazier air permeability of such a paper tissue wrap was measured to be 473 cubic feet per square foot per minute and it had an average superabsorbent shake out of 264 milligrams.

Example 6

In Example 6 a meltblown absorbent core wrap was made in the same fashion as that of Example 5 except that the basis weight was increased to 9.8 grams per square meter. The sample had an average fiber diameter of 3.7 microns with 95 percent of the fibers having fiber diameters below 7 microns. The sample had wet MD and CD peak load tensile strengths of 884 grams and 407 grams respectively. The dry MD and CD peak load tensile strengths were 871 grams and 407 grams respectively and the wet to dry strength ratio in the MD and CD directions were 1.01 and 1.0 respectively. The sample had elongations at peak load of 7 percent in the machine direction and 13 percent in the CD direction. The Frazier air permeability was 397 cubic feet per square foot per minute and the Coulter porometer mean flow pore size was 27 microns. Less than 5 percent of the pores were larger than 50 microns. Using the same shake out test as that for Example 5, the material in Example 6 had no measurable superabsorbent shake out.

Example 7

In Example 7, the meltblown absorbent core wrap was also produced with the same polymer and in the same manner as the previous two examples except that the basis weight was further increased to 12.2 grams per square meter. The average fiber diameter was 4.3 microns with 89 percent of the fibers having fiber diameters less than 7 microns. The sample material had wet MD and CD peak load tensile strengths of 1092 grams and 542 grams respectively. The dry values were 1065 grams in the MD direction and 519 grams in the CD direction. The wet to dry strength ratio in the MD direction was 1.03 and 1.04 in the CD direction. The MD and CD elongation values at peak load were 5 percent and 12 percent respectively and the Frazier air permeability was measured to be 317 cubic feet per square foot per minute. The Coulter porometer mean flow pore size was 28 microns and less than 5 percent of the pores were larger than 50 microns. Shake out using the same test as with respect to Examples 5 and 6 was less than 0.1 milligrams of superabsorbent.

Example 8

In Example 8, the basis weight of the polypropylene meltblown absorbent core wrap was increased to 14.2 grams per square meter with the average fiber diameter being 4.0 microns. The dry MD and CD peak load tensile strengths were 1221 grams and 517 grams respectively and the wet MD and CD peak load tensile strengths were 1238 grams and 530 grams respectively. The ratio of wet to dry strength peak load tensile strengths in the MD and CD directions were 1.01 and 1.03 respectively. The elongation of the sample in the machine direction at peak load was 4 percent and in the cross-machine direction was 6 percent. The Frazier air permeability of the sample was 265 cubic feet per square foot per minute and the Coulter porometer mean flow pore size was 29 microns. Less than 5 percent of these pores were larger than 50 microns. The sample exhibited a shake out of 1.8 milligrams of superabsorbent using the same test procedure as was used for Examples 5 through 7.

Example 9

In Example 9, the same type of meltblown nonwoven web was formed as with the previous examples using the same polymer type. The resultant core wrap had a basis weight of 15.0 grams per square meter and the average fiber diameter was 2.8 microns. The dry MD and CD tensile strengths at peak load were 1512 grams and 701 grams respectively and the MD and CD elongations were 20 and 35 percent. Mean flow pore size was 20 microns and the maximum flow pore size was 31 microns. The Frazier air permeability was 214 cubic feet per square foot per minute and the packet shake-out superabsorbent weight was 6.8 milligrams.

The same material was also used to wrap an absorbent core of 10 grams of the Dow 534 superabsorbent and 10 grams of Kimberly-Clark CR-54 fluff to form an absorbent article. This absorbent article was in turn incorporated into a diaper construction in between a liquid pervious top sheet/body side liner and a bottom sheet or outer cover.

Examples 1 through 9 illustrate several important features of the present invention. The core wrap must provide adequate superabsorbent particle containment yet the same core wrap must provide sufficient air permeability to allow formation of the absorbent core. The examples demonstrate that excellent superabsorbent containment can be achieved with core wrap materials with basis weights of 15 grams per square meter and lower. Generally, this was found to be more achievable if the fiber diameter of the fibers was maintained below 8 microns and the mean flow pore size was maintained below 30 microns. Higher basis weight materials can also be used but this adds additional cost to the overall structure. In addition, higher basis weights can tend to reduce the Frazier air permeability of the material. Frazier air permeability values below 200 cubic feet per square foot per minute make it difficult to form the absorbent core onto the core wrap material.

Having thus described the invention in detail, it should be apparent that various modifications and changes can be made to the present invention without departing from the spirit and scope of the following claims.

We claim:

1. An absorbent article comprising:

an absorbent core including particulate superabsorbent and a fibrous nonwoven web core wrap for containing said particulate, said core wrap comprising a plurality of thermoplastic fibers, said core wrap having a plurality of pores with a mean flow pore size less than about 30 microns and wherein no more than five percent of said plurality of pores have a pore size greater than 50 microns, said core wrap having a wet to dry strength ratio in the machine direction or the cross-machine direction of 0.5 or greater, said core wrap further having a Frazier air permeability of at least 200 cubic feet per square foot per minute.

2. The absorbent article of claim 1 wherein said core wrap has a machine direction elongation at peak load of 30 percent or less.

3. The absorbent article of claim 2 wherein said core wrap has a cross-machine direction elongation at peak load of 40 percent or less.

4. The absorbent article of claim 1 wherein said core wrap has less than 60 milligrams of shake out of particulate superabsorbent.

5. The absorbent article of claim 1 wherein said absorbent core contains a plurality of fibers which are thermally bondable to said core wrap.

6. The absorbent article of claim 1 wherein at least 85 percent of said plurality of fibers in said core wrap have fiber diameters of 8 microns or less.

7. The absorbent article of claim 1 wherein at least 95 percent of said plurality of fibers in said core wrap have fiber diameters of 7 microns or less.

8. The absorbent article of claim 1 wherein no more than one percent of said plurality of pores in said core wrap have a pore size greater than 50 microns.

9. The absorbent article of claim 1 wherein said fibrous nonwoven web core wrap is a polyolefin meltblown fibrous web.

10. A personal care product comprising a top sheet and a bottom sheet with an absorbent article according to claim 1 positioned between said top sheet and said bottom sheet.

11. The personal care product of claim 10 wherein said product is a diaper.

12. The personal care product of claim 10 wherein said product is a sanitary napkin.

13. The personal care product of claim 10 wherein said product is a training pant.

14. The personal care product of claim 10 wherein said product is an incontinence garment.

15. A process for forming an absorbent article comprising:

forming a fibrous nonwoven web core wrap by extruding a molten thermoplastic polymer into a plurality of molten streams, attenuating said plurality of molten streams into a plurality of fibers and depositing said plurality of fibers onto a forming surface to form a fibrous nonwoven web core wrap having a plurality of pores with a mean flow pore size of less than about 30 microns with no more than five percent of said plurality of pores having a pore size greater than 50 microns and with said fibrous nonwoven web core wrap having a wet to dry strength ratio in the machine direction or the cross-machine direction of 0.5 or greater and a Frazier air permeability of at least 200 cubic feet per square foot per minute, depositing a quantity of particulate superabsorbent onto said core wrap, and sealing said core wrap to envelope said particulate superabsorbent.

16. The process of claim 15 which further includes the step of depositing a plurality of absorbent fibers onto said core wrap prior to said sealing step.

* * * * *